United States Patent [19]
Cella et al.

[11] 3,993,745
[45] Nov. 23, 1976

[54] PERFLUORINATED COMPOUNDS IN HAIR TREATMENT COMPOSITIONS

[75] Inventors: John A. Cella, Plandone Mills, N.Y.; Robert A. Lukey, Northbrook, Ill.; August Emil Fiebig, Jr., Chicago, Ill.; Frank J. Pum, Glen Ellyn, Ill.

[73] Assignee: Alberto Culver Company, Melrose Park, Ill.

[22] Filed: May 31, 1974

[21] Appl. No.: 474,956

[52] U.S. Cl. .............................. 424/71; 424/DIG. 1; 424/DIG. 2; 424/47; 424/70; 424/78; 424/80; 424/81
[51] Int. Cl.² ............................................ A01K 4/11
[58] Field of Search ............ 260/556 F; 424/DIG. 1, 424/DIG. 2, 70, 71, 47, 78, 80, 81

[56] References Cited
UNITED STATES PATENTS

| | | |
|---|---|---|
| 2,759,019 | 8/1956 | Brown et al. ..................... 260/556 F |
| 2,803,656 | 8/1957 | Ahlbrecht et al. .............. 260/556 F |
| 2,809,990 | 10/1957 | Brown .................................. 260/534 |
| 2,915,554 | 12/1959 | Ahlbrecht et al. .............. 260/556 F |
| 3,147,064 | 9/1964 | Brown et al. ......................... 8/116.2 |
| 3,147,066 | 9/1964 | Brown et al. ......................... 8/116.2 |
| 3,217,035 | 11/1965 | Lazerte et al. .................. 260/556 F |
| 3,245,817 | 4/1966 | Lovness .............................. 106/279 |
| 3,708,537 | 1/1973 | Groves ............................ 260/556 F |

*Primary Examiner*—Albert T. Meyers
*Assistant Examiner*—Vera C. Clarke
*Attorney, Agent, or Firm*—Wallenstein, Spangenberg, Hattis & Strampel

[57] ABSTRACT

Hair setting lotions, gels, hair sprays and grooming aids, containing distinctly minor proportions of hydrophobiclipophobic perfluorinated compounds.

12 Claims, No Drawings

PERFLUORINATED COMPOUNDS IN HAIR TREATMENT COMPOSITIONS

Our invention is directed to improved hair setting lotions, gels, hair sprays and grooming aids for the treatment of hair on the human head.

It has long been known that the sebaceous glands in the human scalp substantially continuously secrete sebum which acts to keep the hair lubricated, smooth and shiny. It has also long been known that many people suffer from an overproduction of sebum and, as a result, have oily hair. Oily hair readily picks up dust and other particulate matter from the environment which results in the hair becoming soiled and sticky, a situation which requires frequent hair shampooing, commonly as often as every day or every other day, in order to make the hair look clean and presentable.

The secretion products of the sebaceous glands, especially if produced in excess, frequently have an adverse effect on certain hair care products which are applied to the live human hair to impart desirable properties thereto in relation to texture, hold and general appearance. Hair setting lotions, gels, hair sprays and grooming aids are most generally adversely affected by the sebum or natural oils secreted by the sebaceous glands. In this connection, it may be noted that the aforesaid hair treatment products contain resins which may be of nonionic, anionic, cationic and amphoteric character. The sebum or natural oils tend to plasticize the resins with the result that the desired properties of the resins are adversely affected, resulting in diminishing or loss of the holding power of the resins. The adverse effects of the sebum or natural oils secreted by the sebaceous glands greatly depend on the physiological activity and are, therefore, dependent on the individual and a function of time. Highly active sebaceous glands will show the adverse effects in a much shorter time than glands of normal or low activity.

We have found that the incorporation into hair setting lotions, gels, hair conditioners and grooming aids of distinctly minor amounts of certain compounds not only does not adversely affect their effectiveness but, indeed, enhances their effectiveness in that it substantially reduces the excess flow of the sebum or sebaceous secretions by treatment of the hair with said hair treatment compositions.

The aforementioned chemical compounds which are incorporated into the aforesaid hair treatment compositions of our present invention are hydrophobic-lipophobic perfluorinated compounds which can be represented by the formula $$CF_3-(CF_2)_x-(CH_2)_y-Z$$

where Z is a water or oil solubilizing group of either organic or inorganic character, $x$ is an integer which is generally from 2 to 17, particularly from 7 to 11, and $y$ is an integer from 0 to 4, and said compounds may be anionic, cationic, nonionic or amphoteric, depending upon the nature of the grouping or groupings encompassed by Z. The Z groups may be or may comprise sulfonic, sulfate, phosphate, amide, alkyl-substituted amide, sulfonamido, carboxylic, quaternary ammonium, betainic and similar groups. The hydrophobic-lipophobic perfluorinated compounds are per se known to the art and are identified by trademarks such as the FLUORADS (Minnesota Mining and Manufacturing Company) and ZONYLS (E. I. du Pont de Nemours & Company). The water solubility and organic solvent solubility of the aforesaid compounds are, as is known, affected and can be controlled by varying the chain length of the perfluorinated hydrocarbon moiety and by the selection of Z as designated in the above mentioned general formula.

Illustrative samples of the hydrophobic-lipophobic perfluorinated compounds are the following:

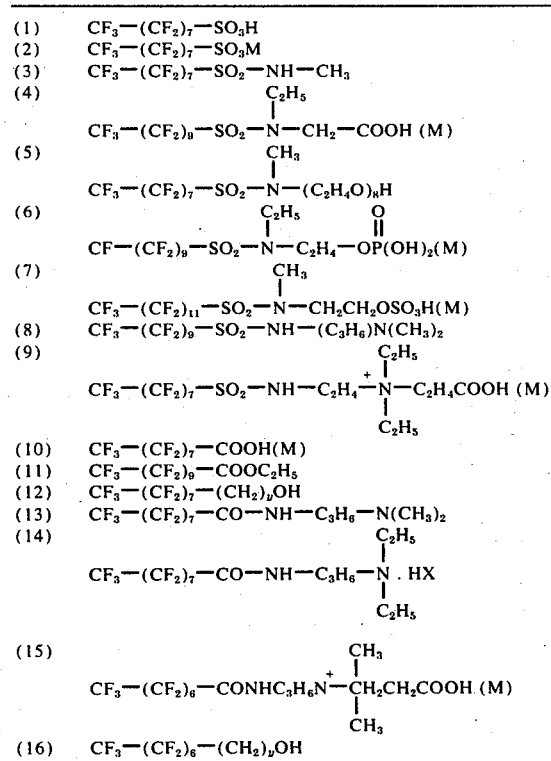

-continued

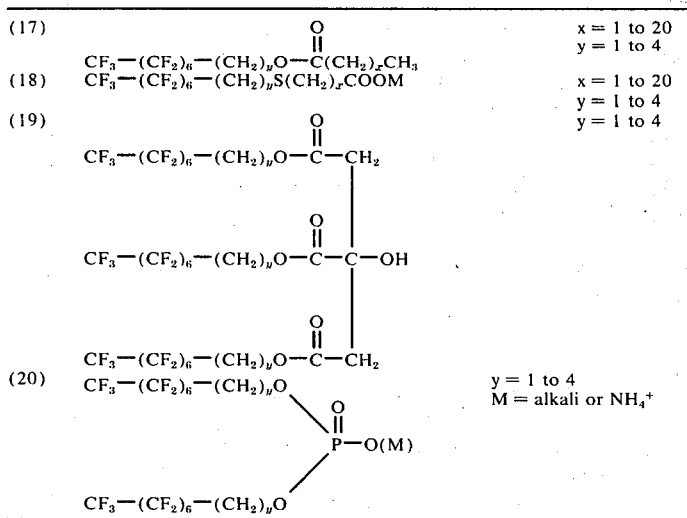

The aforesaid hydrophobic-lipophobic perfluorinated compounds are effective, in the aforesaid hair treatment compositions of our present invention, in very low concentrations, as low as 0.05%, by weight of the hair treatment compositions, to of the order of about 1% or 2% or slightly higher. As a general rule, proportions of the order of about 0.1% to 1% are generally adequate, with a good general average being about 0.1% to 0.5%. The lower limit is determined by the particular efficacy of the specific compounds in selected hair setting lotions, gels, hair sprays and grooming aid compositions, whereas the upper limit, not in excess of 10%, is usually governed by somewhat similar considerations except that, generally speaking, no more should be used than is necessary and, in addition, it is desirable not to exceed the solubility or ready dispersibility limits of the compound in the particular aforesaid types of hair treating composition involved, while maintaining homogeneity in said compositions.

The hydrophobic-lipophobic perfluorinated compounds can be incorporated in a great variety of hair setting lotions, hair styling gels, hair sprays and hair grooming compositions. In all these resin-containing products the hydrophobic-lipophobic perfluorinated compound serve to inhibit or delay the plasticizing effects of the sebum or sebaceous secretions on the resin. Moreover, since many of the resins used in the above mentioned products, such as resins of the cellosize or polyvinylpyrrolidone type, are hygroscopic and tend to lose their holding power under humidity conditions, inhibition of the pick-up of atmospheric moisture is achieved to a substantial extent by the practice of the present invention, resulting in significantly prolonging the holding power of the aforesaid hair treatment compositions formulated with hygroscopic types of resins.

The compositions generally contain an organic solvent, commonly a lower molecular weight alcohol which is soluble in or at least partially miscible with water. The organic solvents include, by way of illustration, ethanol, isopropanol, Carbitol, acetone, and the like, or compatible mixtures, especially advantageous being ethanol. Where water-organic solvent mixtures are used, for instance, water-ethanol or water-isopropyl alcohol, the water content of the compositions will commonly fall within the range of about 10% to about 80%, by weight, of the compositions. Generally, the compositions will contain from about 15% or 20% to about 96%, by weight of the compositions, of an organic solvent or mixture of organic solvents, with or without water, and the latter may be present in the organic solvent as, for instance, where 95% ethanol is employed, or may be added extraneously, or the compositions may be free or essentially free from water. In the case of hair sprays, it is especially desirable that they contain from 90 to 96% of ethanol (or conventional 95% ethanol), usually about 95% of ethanol, by weight of the hair sprays. The pH of the compositions may vary from 2.5 to 9. However, a pH between 4.7 and 7.5 is the range of choice. The compositions may also contain supplemental ingredients, generally in quite minor proportions, including, for instance, desired perfume and color.

The resins which are included in the compositions of our present invention can be selected from a wide group which includes those commonly utilized in setting lotions, gels, hair sprays and grooming aids, illustrative examples of which are those of the cellosize and polyvinylpyrrolidone types, quaternized polyvinylpyrrolidones, amphoteric acrylic resins, carboxy vinyl polymers, and others as well. The proportions thereof are variable but, in all instances, are distinctly minor in amount, commonly ranging from about 1% to about 7%, advantageously about 4% to about 6%, by weight of the compositions, but there is nothing critical about said proportions.

The following examples are illustrative but in no way limitative of the invention since many other hair treatment compositions of the aforesaid types can readily be made in light of the guiding principles and teachings contained herein. All percentages listed are by weight, unless otherwise specifically stated.

EXAMPLE 1

| Hair Setting Lotion | |
|---|---|
| Quaternized PVP | 1.00 |
| Ammonyx 4002[1] | 0.20 |
| Hyamine 1622[2] | 0.10 |
| Ethanol SDA-40 | 20.00 |
| Compound of Structure 10 | 2.00 |
| Water | 76.50 |

-continued

| Hair Setting Lotion | |
|---|---|
| Perfume | 0.20 |
| | 100.00% |

[1]Stearyldimethylbenzyl Ammonium Chloride
[2]Di-Isobutyl Phenoxy Ethoxy Ethyl Dimethylbenzyl Ammonium Chloride In the preparation of the hair setting lotion of this Example 1, it is convenient to disperse the quaternized PVP in the water at room temperature. The Ammonyx 4002, Hyamine 1622 and the perfume are dissolved in the ethanol and the resulting mixture is added to the previously prepared aqueous dispersion of the quaternized PVP, under conditions of stirring. Then, while still stirring, the compound of structure 10 is added.

Mixing procedures for other hair setting lotions, hair sprays and hair grooming aids of the present invention, illustratively disclosed in the following Examples, will be apparent to those skilled in the art.

EXAMPLE 2

| Hair Setting Lotion | |
|---|---|
| Gantrez ES-425[3] | 3.00 |
| Ethoxylated Lanolin Derivative | 0.20 |
| Ethanol SDA-40 | 20.00 |
| Compound of Structure 18 | 0.10 |
| Perfume | 0.05 |
| Water | 76.65 |
| | 100.00% |

[3]Monobutylester of Poly(methylvinylether) Maleic Acid (S.G. 0.977)

EXAMPLE 3

| Hair Setting Gel | |
|---|---|
| PVP Type NP K30 | 1.50 |
| Glycerine | 1.50 |
| Carbopol 940[4] | 0.50 |
| Ethanol SDA-40 | 20.00 |
| Diisopropanolamine | 0.35 |
| Compound of Structure 20 | 1.00 |
| Perfume | 0.15 |
| Water | 75.00 |
| | 100.00% |

[4]Carboxy vinyl polymer

EXAMPLE 4

| Hair Spray (Concentrate) | |
|---|---|
| PVP K30 (50%) | 5.00 |
| Ethanol | 94.75 |
| Compound of Structure 7 | 0.10 |
| Perfume | 0.15 |
| | 100.00% |

EXAMPLE 5

| Hair Spray (Concentrate) | |
|---|---|
| Amphomer (2849-10)[5] | 2.50 |
| Diisopropanolamine | 0.34 |
| Ethanol | 96.91 |
| Compound of Structure 4 | 0.10 |
| Perfume | 0.15 |
| | 100.00% |

[5]Amphoteric Acrylic Resin

EXAMPLE 6

| Hair Spray (Concentrate) | |
|---|---|
| Gafquat 734 (50%)[6] | 5.00 |
| Ethanol | 94.75 |
| Compound of Structure 15 | 0.10 |
| Perfume | 0.15 |
| | 100.00% |

[6]Quaternized Vinyl Pyrrolidone Copolymer

EXAMPLE 7

| Hair Spray (Concentrate) | |
|---|---|
| Ethanol | 93.48 |
| 2-methyl-2-aminopropanol | 0.19 |
| Gantrez ES-425 (50%) | 6.00 |
| Compound of Structure 6 | 0.1 |
| Perfume | 0.23 |
| | 100.00% |

EXAMPLE 8

| Hair Spray (Concentrate) | |
|---|---|
| Ethanol | 93.80 |
| Gantrez ES-425 (50%) | 5.00 |
| 2-methyl-2-aminopropanol | 0.10 |
| Compound of Structure 10 | 1.00 |
| Perfume | 0.10 |
| | 100.00% |

EXAMPLE 9

| Hair Grooming Aid | |
|---|---|
| Ucon LB-625[7] | 15.50 |
| Ethanol SDA-40 | 70.80 |
| Water | 10.10 |
| Amphomer (28-4910) | 2.00 |
| 2-amino-2-methylpropanol | 0.35 |
| Perfume | 0.15 |
| Compound of Structure 6 | 1.10 |
| | 100.00% |

[7]Polyalkylene Glycols

The compositions of the present invention can be packaged in conventional non-pressurized containers or, if desired, certain of them, particularly the hair sprays, can be and desirably are packaged in aerosol containers utilizing known or conventional propellants. The proportions of ingredients recited above and in the claims are exclusive of the propellants in those cases in which the compositions, as packaged, are admixed with propellants as in aerosol-packaged compositions.

We claim:

1. A composition, for treating live human hair selected from the class consisting of a hair setting lotion, a hair setting gel and a hair spray, which includes, as ingredients thereof, a resin, a solvent, and a hydrophobic-lipophobic compound of anionic, cationic, nonionic or amphoteric character corresponding to the formula $$CF_3-(CF_2)_x-(CH_2)_y-Z$$

where Z is a member selected from the class consisting of a water-solubilizing group and an oil-solubilizing group, $x$ is an integer from 2 to 17, and $y$ is an integer from 0 to 4, said compound being present in proportions, based on the weight of the composition, in the range of about 0.05% to not in substantial excess of the solubility or ready dispersibility of said compound in the composition and not in excess of 10%.

2. The composition of claim 1, in which the proportions of said compound are in the range of about 0.1% to about 1%.

3. The composition of claim 1, in which the solvent is a single solvent or mixture of solvents and is present in an amount in the range of about 1% to about 96% by weight of said composition.

4. The composition of claim 3, in which the solvent is a water-soluble lower molecular weight aliphatic alcohol.

5. The composition of claim 4, in which the alcohol is a member selected from the group consisting of ethanol and isopropyl alcohol.

6. The composition of claim 1, in which, in the hydrophobic-lipophobic compound, $x$ is 7 to 11.

7. The composition of claim 1, in which Z is a member selected from the class consisting of sulfonic, sulfate, carboxyl, phosphate and quaternary ammonium groups.

8. The composition of claim 6, in which the hydrophobic-lipophobic compound is anionic in character.

9. The composition of claim 6, in which the hydrophobic-lipophobic compound is cationic in character.

10. The composition of claim 6, in which the hydrophobic-lipophobic compound is amphoteric in character.

11. The composition of claim 6, in which the hydrophobic-lipophobic compound is nonionic in character.

12. A hair setting lotion comprising a solvent, from about 1% to 7% of a hair treating resin and the hydrophobic-lipophobic compound of anionic, cationic, nonionic or amphoteric character corresponding to the formula set forth in claim 1, said compound being present in proportions, based on the weight of the lotion, in the range of about 0.05% to about 2%.

* * * * *